(12) United States Patent
Parker et al.

(10) Patent No.: US 8,733,551 B2
(45) Date of Patent: May 27, 2014

(54) MEDICAL EQUIPMENT STORAGE AND TRANSPORTATION KIT

(75) Inventors: George Christopher Parker, Westcliff-on-Sea (GB); Barry Luke, Canvey Island (GB)

(73) Assignee: Medicart International Limited (GB)

( * ) Notice: Subject to any disclaimer, the term of this patent is extended or adjusted under 35 U.S.C. 154(b) by 179 days.

(21) Appl. No.: 13/122,739

(22) PCT Filed: Oct. 21, 2008

(86) PCT No.: PCT/GB2008/050972
§ 371 (c)(1),
(2), (4) Date: Apr. 6, 2011

(87) PCT Pub. No.: WO2010/046617
PCT Pub. Date: Apr. 29, 2010

(65) Prior Publication Data
US 2011/0192744 A1    Aug. 11, 2011

(51) Int. Cl.
*B65D 85/00* (2006.01)
(52) U.S. Cl.
USPC .......................................... 206/570; 206/438
(58) Field of Classification Search
USPC ............... 206/570, 438, 571, 557; 220/666, 6
See application file for complete search history.

(56) References Cited

U.S. PATENT DOCUMENTS

| | | | |
|---|---|---|---|
| 3,353,664 A | 11/1967 | Armentrout et al. | |
| 4,106,621 A * | 8/1978 | Sorenson | 206/365 |
| 4,226,328 A | 10/1980 | Beddow | |
| 5,209,392 A * | 5/1993 | Anatro | 229/117.01 |
| 5,492,671 A * | 2/1996 | Krafft | 422/26 |
| 5,615,639 A * | 4/1997 | Knight | 119/168 |
| 6,206,192 B1 * | 3/2001 | Winstead et al. | 206/572 |
| 6,364,203 B2 * | 4/2002 | Toussant et al. | 229/407 |
| 6,749,063 B2 * | 6/2004 | Parker | 206/363 |
| 7,163,340 B2 * | 1/2007 | Godshaw et al. | 383/121 |
| 7,229,001 B2 * | 6/2007 | Wang | 229/117.05 |
| 7,445,120 B2 * | 11/2008 | Brej | 206/747 |
| 7,878,356 B2 * | 2/2011 | Gartz et al. | 220/4.22 |
| 8,439,215 B2 * | 5/2013 | Gartz et al. | 220/4.22 |
| 2001/0000480 A1 * | 4/2001 | Stagg et al. | 428/43 |
| 2003/0080125 A1 * | 5/2003 | Cassani | 220/6 |
| 2003/0159966 A1 * | 8/2003 | McMichael et al. | 206/570 |
| 2005/0236415 A1 * | 10/2005 | Ozasa et al. | 220/912 |
| 2006/0011506 A1 * | 1/2006 | Riley | 206/570 |
| 2006/0042977 A1 | 3/2006 | Sandel | |

(Continued)

FOREIGN PATENT DOCUMENTS

| | | |
|---|---|---|
| DE | 29608617 | 8/1996 |
| EP | 0308900 | 3/1989 |
| WO | 2007049076 | 5/2007 |

*Primary Examiner* — Steven A. Reynolds
(74) *Attorney, Agent, or Firm* — Renner Kenner Greive Bobak Taylor & Weber

(57) ABSTRACT

A kit for the storage and transportation of medical equipment (31) following processing or use thereof contains, as its principal component, a tray (10) defined by a base (12) and surrounding walls (13, 14). The tray (10) has at least one fold line (19) formed in the base and/or walls (13, 14), thereby to facilitate compaction of said tray (10) for disposal. Optional further components of the kit include: a tray line (28); a protective cover (34) adapted to be detachably secured to the tray (10); a lid (23) adapted to engage with the walls (13, 14) of the tray (10); and an oxygen-impermeable container (37) adapted to receive said tray (10) therewithin.

18 Claims, 5 Drawing Sheets

(56) References Cited

U.S. PATENT DOCUMENTS

| | | | |
|---|---|---|---|
| 2006/0071002 A1* | 4/2006 | Hurst | 220/345.1 |
| 2007/0017921 A1* | 1/2007 | Carmona | 220/666 |
| 2007/0284422 A1* | 12/2007 | Saunders et al. | 229/101 |
| 2008/0197177 A1* | 8/2008 | Volz et al. | 229/101.2 |
| 2008/0203100 A1* | 8/2008 | Young | 220/574 |
| 2010/0095899 A1* | 4/2010 | Lipscomb et al. | 119/167 |
| 2010/0205850 A1* | 8/2010 | Bernard | 43/131 |
| 2013/0056387 A1* | 3/2013 | Numata et al. | 206/557 |

\* cited by examiner

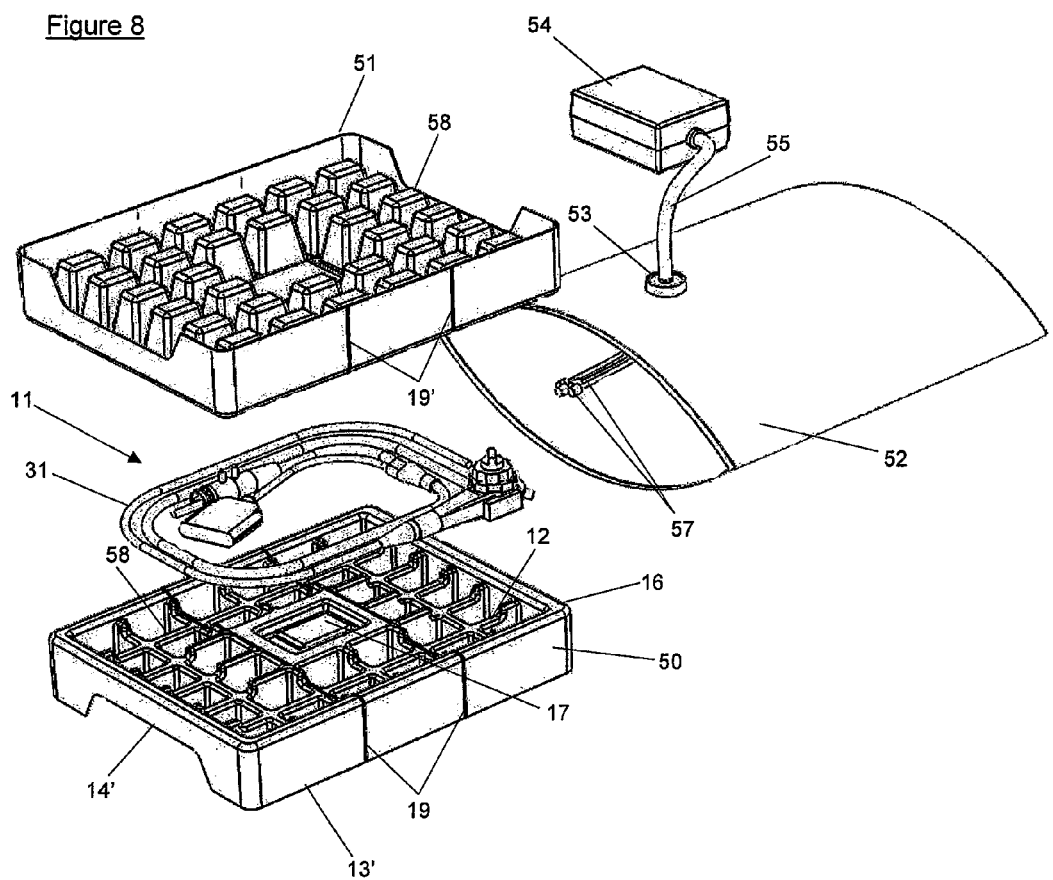

MEDICAL EQUIPMENT STORAGE AND TRANSPORTATION KIT

This invention relates to a kit of parts for the storage and transportation of medical equipment, and to a method for maintaining the disinfection of medical equipment utilising such a kit of parts.

The present invention has been developed in connection with the storage and transportation of flexible medical endoscopes, and therefore will be described herein with particular emphasis on this application. It is envisaged however, that the apparatus and method of the present invention may be applied to the storage and transportation of substantially all types of medical, surgical, dental and veterinary equipment, apparatus, and instruments.

After use in a surgical procedure, articles of medical equipment such as endoscopes are usually subjected to a rigorous cleaning and disinfecting procedure known as "processing", before being stored in a clean environment. Such processing generally requires the use of washers, disinfectors, automated sterilisers for heat sensitive equipment, ultra-sonic cleaners and autoclaves for non-heat sensitive equipment. Some of this apparatus may be located in the same area as that in which the medical equipment is used, but good practice generally dictates that the processing be carried out in a separate dedicated facility.

Recent trends in healthcare, particularly in the UK, have seen a marked increase in the "out-sourcing" of many associated services, including the processing of medical equipment. Processing is now often carried out in large regional processing centres dedicated to cleaning, disinfection and sterilisation of a wide range of equipment from hospitals and clinics within a defined geographical region. Ideally, the regional processing centre will be in fairly close proximity to hospital and clinics requiring the equipment. However, this is seldom likely to be the case for all hospitals and clinics in the area, and this results in the equipment having to be transported over relatively long distances.

The remote location of such regional processing centres relative to the hospitals and clinics where the equipment is required causes a particular problem with regard to flexible medical endoscopes. These, and other sensitive articles of medical equipment, need to be processed to, and maintained at, a high level of disinfection. There is therefore a time limitation between completion of processing and subsequent use of the equipment, within which the level of disinfection can be maintained at a satisfactory level. In the case of flexible endoscopes, the British Society of Gastroenterology (BSG) cleaning and disinfection guidelines specify that a period of no more than 3 hours should elapse between completion of processing and time of use. This is due to the multiplication of residual pathogens which may remain on the equipment after disinfection, or which may be present in the atmosphere. If the equipment is not used in a further procedure within this time, then further cleaning and disinfection will be necessary prior to its next use.

Even when the regional processing centre is within close proximity to the area in which the equipment will be used, implementation of this "3 hour rule" often results in the re-processing of unused equipment. Where the regional processing centre is remote from the hospital or clinic where the endoscope is to be used, the 3 hour time limit is likely to be practically impossible to meet, and this leads to the risk of surgical procedures being carried out using equipment at an unsatisfactory level of disinfection.

The present invention seeks to address this issue by providing a low cost kit for the storage and transportation of medical equipment, and by providing a method for maintaining the disinfection of medical equipment utilising such a kit. It is envisaged that the kit and method of the present invention will enable a significant increase in the viable disinfected storage time of flexible medical endoscopes, and other medical equipment so as to avoid the unnecessary and costly re-processing of unused equipment, and the danger of equipment being used at an unsatisfactory level of disinfection.

A device for the storage and transportation of flexible medical endoscopes is disclosed in the applicant's European Patent No. 1,439,795. A method for maintaining the disinfection of flexible medical endoscopes is disclosed in the applicant's International Publication No. WO 2007/049076. These articles of prior art address a number of issues arising in relation to the use, processing, storage and transportation of medical equipment in general, and flexible medical endoscopes in particular. However, certain other issues remain unaddressed, or have arisen since the filing of the above applications.

For example, the identification of the disinfection status of medical equipment in a busy hospital department is known to be a problem, despite the strict processing guidelines. In endoscopy in particular, there are known instances of contaminated endoscopes mistakenly being used on patients, which is clearly unacceptable due to the risk of infection.

Furthermore, the levels of disinfection achieved and maintained may at present be limited by the repeated processing of storage and transportation devices along with the medical equipment being processed. Methods for the processing of medical equipment as presently utilised by hospital departments and processing centres are also notable for the lack of any specific steps aimed at prolonging the period for which medical equipment can be maintained at a satisfactory level of disinfection.

The present invention seeks further to address these issues by providing an improved, low cost kit for the storage and transportation of medical equipment, and to provide an improved method for maintaining the disinfection of medical equipment. In particular, the present invention seeks to provide improvements in relation to the identification of medical equipment as being either clean or contaminated, and the levels of disinfection achieved and maintained.

According to a first aspect of the present invention, there is provided a kit of parts for the storage and transportation of medical equipment following processing or use thereof, said kit comprising:

a tray defined by a base, and surrounding wall(s), said tray having at least one fold-line formed in the base and/or wall(s), thereby to facilitate compaction of said tray for disposal;

and optionally one or more of:

a tray liner;

a protective cover adapted to be detachably secured to the tray;

a lid adapted to engage with the wall(s) of the tray; and an oxygen-impermeable container adapted to receive said tray therewithin.

In a first major embodiment of a kit of parts according to the first aspect of the present invention, the tray has an inner compartment defined by the base and surrounding wall(s), and peripheral lip-portion(s) provided at least partially around said wall(s); the tray liner, if present, is adapted to line the inner compartment of the tray; and the protective cover, if present, is adapted to be extended across the inner compartment. The inner compartment of the tray is preferably downwardly-dished, with the surrounding wall(s) upstanding from the base. The peripheral lip-portion(s) preferably extend outwardly from the surrounding wall(s).

The tray liner (if present) is preferably formed of a flexibly deformable sheet material such that in use said tray-liner is arranged to overlie the tray.

The protective cover (if present) is preferably adapted to be detachably secured to the tray so as safely to enclose and protect medical equipment therewithin.

The lid (if present) preferably has tapered edges adapted to engage with complementary tapered edges provided on the wall(s) of the tray.

It is envisaged that there may be circumstances, particularly following use of medical equipment in a surgical procedure, when the tray will be utilised alone without the liner. However, where sterility is required—and in particular, when delivering clean medical equipment from the processing centre to the procedure room or operating theatre—it is highly desirable that the liner, and preferably also the cover be used. More preferably the lid, and most preferably also the container, are utilised in addition to the liner and cover.

As will be apparent from the foregoing statement of invention, the liner, lid, cover and container are optional, though preferred, components of the present invention which will not necessarily be present in each embodiment. References herein to "the tray and the lid", or similar, should therefore be construed accordingly as meaning "the tray (and the lid, if present)", or similar.

In order to address the present invention's aims of providing a low cost kit of parts which is capable of maintaining high levels of disinfection, it is highly preferable that the tray, and any associated peripherals, should be single use, disposable items. The cost benefits of a disposable kit are clear, in that less expensive materials can be used for the construction of components of the kit since durability is not a requirement. Making the components of the kit disposable also enhances the level of disinfection achievable, since a fresh kit will be used each time an article of medical equipment emerges from processing, with no need for the components themselves to be cleaned after use, as they will instead simply be disposed of.

The at least one fold-line formed in the tray is provided with the aim of facilitating disposal of the tray after use. The fold-line will be formed as a weakened region, preferably extending horizontally across the base and vertically up a pair of opposed side walls at each side thereof.

The lid is preferably formed with a similar construction to that of the tray, having at least one fold-line formed therein. More preferably, the tray and the lid each have two, or most preferably three, fold-lines formed therein.

Each fold-line is preferably provided with reinforcement means located adjacent thereto, so as to maintain the rigidity of the tray or lid respectively, when in use. Each said reinforcement means preferably comprise a removable tab and an associated cut-out section, located at each end of each said fold-line. When the tray or lid is to be disposed of, this is carried out by breaking off the removable tab, thus allowing access to the cut-out section to enable manual folding or breaking of the tray or lid along the fold-line(s).

As noted above, the present invention has been developed particularly for the storage and transportation of flexible medical endoscopes. It is therefore highly preferable that the tray be provided with at least one island structure upstanding from the base, and preferably formed integrally therewith. The islands structure provides support for the tube of the endoscope, which can be carefully coiled around the island structure to prevent damage during transit. The island structure provides the further benefit of reducing air space inside the tray. This has advantages when the kit of parts of the first aspect of the present invention is utilised in a method according to a second aspect of the present invention. As will be described in more detail below, said method involves a step of wholly or partially evacuating the tray in order to remove oxygen and moisture from the inner compartment, so as to reduce or eliminate the multiplication of aerobic micro-organisms. In a preferred sub-embodiment of the first major embodiment, the tray is provided with two inter-connected island structures.

As also noted above, the present invention seeks also to provide improvements in the identification of the disinfection status of medical equipment (i.e. whether the equipment is clean or contaminated) before and after use of the equipment in a medical procedure. To this end, the kit of parts of the present invention preferably comprises a pair of interchangeable protective covers, one member of said pair of covers carrying an indicator adapted to provide a visual indication that medical equipment contained within said inner compartment is clean, and the other member of said pair carrying an indicator adapted to provide a visual indication that said medical equipment is contaminated. The visual indications may simply be the words 'CLEAN' and 'CONTAMINATED' or similar, and/or may involve all or part of the cover carrying an appropriate colour coding such as green for clean and red for contaminated.

In an alternative embodiment of the present invention, a single reversible cover may be provided, carrying the above described visual indications of disinfection status on opposed faces thereof.

To facilitate application of the cover(s) onto the tray, and the subsequent removal of the cover(s) from the tray, it is preferred that each cover is provided with manually graspable 'ears' at the corners thereof.

A further improvement in disinfection status identification may be achieved by the provision, within the kit of the present invention, of one or more disinfection status indication tags adapted for attachment to medical equipment within the tray, said tags being adapted to provide a visual indication as to whether said medical equipment is clean or contaminated. As with the covers described above, the visual indications may simply be the words 'CLEAN' and 'CONTAMINATED' or similar, or may involve all or part of the tag carrying an appropriate colour coding such as green for clean and red for contaminated.

Preferably, the kit comprises one or more 'clean' status indication tags for attachment to medical equipment following processing, and one or more 'contaminated' status indication tags for attachment to medical equipment following use. In a preferred embodiment of the present invention, said one or more 'clean' status indication tags are attached to, or formed integrally with, said tray liner.

The status indication tags serve to provide a visual indication of the disinfection status of the medical equipment when the cover of the kit of the present invention is removed or absent. Thus, by utilising the kit of the present invention, instances of contaminated endoscopes being mistakenly used on patients may be reduced or eliminated.

In order further to address the present invention's above noted aim of providing a kit comprised of disposable components, it is preferred that each of the tray and the lid are formed from paper pulp material. Most preferably, the paper pulp may be treated with, or comprise, an additive, such as a plasticiser, in order to render the material water resistant. Forming the tray and lid from paper pulp material has significant advantages in relation to the disposability of the components of the kit, since the used components will be suitable for disposal in standard hospital macerators, or alternatively for recycling or incineration.

Although forming the tray and the lid from paper pulp material is the preferred option in terms of making the components of the kit disposable, forming the entirety of the tray and the lid from this material would have the drawback that users would not be able to identify the disinfection status of the equipment within the tray when the lid was in place. Removing the lid in order to inspect the status of the contents is clearly undesirable since it could potentially expose clean equipment to contamination. Therefore, in an alternative embodiment of the present invention, at least one of the tray and the lid are formed wholly or partially from transparent plastics material. In one currently preferred embodiment of the present invention, the tray is formed from paper pulp material, whilst the lid is formed from, or provided with a region formed from, transparent plastics material.

Alternatively, where the lid is formed from paper pulp material, the cover may fit over said lid, rather than vice versa.

Most preferably, the material from which the tray and lid are formed is impregnated with an antibacterial, biocidal or biostatic agent, in order further to increase the levels of disinfection achievable when using the present invention.

In a second major embodiment of a kit of parts according to the first aspect of the present invention, the dimensions of the lid are substantially equal to those of the tray, and the lid is formed with a structure and profile complementary to that of the tray, such that when the lid is engaged with the tray, each said component constitutes substantially one half of a tray assembly, an inner compartment adapted to receive an article of medical equipment being defined between said tray and said lid.

Each of said tray and said lid is preferably provided with at least one island structure. Said island structures may be formed as complementary 'mirror images' of one another, so as effectively to form one continuous structure when the lid is engaged with the tray to form the tray assembly. Preferably, each of the tray and the lid is formed with a cellular structure to impart rigidity to the tray assembly when in use, but to facilitate compaction following use.

The oxygen-impermeable container is preferably provided with a port adapted to communicate with the inner compartment of the tray assembly via at least one or more flexible tubes. To this end, at least one wall of said tray and/or said lid being shaped so as to permit access of said one or more flexible tubes to said inner compartment when the lid is engaged with the tray. The one or more flexible tubes are preferably adapted to communicate with the internal channels of a flexible medical endoscope housed within the inner compartment of the tray assembly, whilst the port provided in the container is preferably adapted to communicate with the ambient atmosphere, thereby permitting aspiration of the internal channels of said endoscope. To avoid contamination of the endoscope channels, said container port is provided with a high efficiency particulate air (HEPA) filter.

The kit of parts according to said second major embodiment preferably further comprises a control module in communication with said container port and adapted to monitor and control the environment within said container. Most preferably, the control module is adapted to communicate with hospital or clinic computer systems, and/or hand held data capture and/or storage devices. This communication may be effected by data cable, wireless networks, optical fibres, or other means.

As noted above, the present invention seeks also to provide an improved method of maintaining the disinfection of medical equipment which, it is envisaged, will significantly extend the period within which medical equipment can be maintained at a satisfactory level of disinfection between processing and use.

Therefore, according to a second aspect of the present invention there is provided a method for maintaining the disinfection of medical equipment following processing thereof, comprising the following major steps:

(a) placing disinfected medical equipment in a tray constituting a principal component of a kit of parts according to the first aspect of the present invention as hereinbefore described;

(b) placing said loaded tray in an oxygen-impermeable container;

(c) sealing the container;

(d) reducing pressure within the container by mechanical, electrical or manual suction; and (e) removing atmospheric oxygen from the container by means of a gas scavenger.

As will be appreciated, the oxygen-impermeable container in step (b) above may be a further component of the kit of parts according to the first aspect of the present invention, as hereinbefore described. As will also be appreciated, the kit of parts utilised in the method according to the second aspect of the present invention may preferably also include the liner, lid, cover and other preferred components of kit of parts according to the first aspect of the present invention as hereinbefore described.

The reduction of pressure in step (d) is preferably carried out to a level where approximately 80% of the air is removed from the container. In addition to removing much of the oxygen required by aerobic micro-organisms, the reduction of pressure also promotes vaporisation of residual moisture, which is required by micro-organisms as a solvent for nutrients. The absence of oxygen and moisture has a further advantage in that it inhibits the corrosion of the medical equipment in the tray.

The gas scavenger in step (e) is preferably provided in sachets within the tray. The scavenger acts to absorb oxygen within the compartment until the oxygen level is reduced to approximately 0.1%. This severely inhibits the ability of any aerobic micro-organisms to multiply. Suitable materials for use as oxygen scavengers include finely-divided iron powders, such as those sold under the trademark ATCO. The gas scavenger sachets may preferably also contain activated carbon and/or a desiccant, to absorb any moisture vapour produced as the pressure is reduced.

The method according to the second aspect of the present invention preferably further comprises one or both of the following additional or preliminary steps:

(i) prior to performing major step (a), the preliminary step of attaching to the medical equipment one or more status indication tags to provide a visual indication that said medical equipment is clean; and/or (ii) prior to performing major step (e), the additional step of charging the container with a disinfectant gas or vapour;

As will be appreciated, the one or more status indication tags in step (i) above may be a further component of the kit of parts according to the first aspect of the present invention, as hereinbefore described.

The disinfectant gas or vapour in step (ii) above permeates through the internal channels of the equipment in order to provide a disinfected atmosphere therein. The disinfectant gas or vapour preferably comprises sterile isopropanol gas in aerosol form. Alternatively, dry nitrogen or vapour phase hydrogen peroxide (VPHP) may be used.

The method according to the second aspect of the present invention preferably also comprises, following use of the medical equipment in a medical procedure and/or the subsequent transportation of said equipment for processing, the further major steps of:

(f) compacting the tray and lid by folding along each said fold-line; and (g) disposing of the compacted tray and lid.

As will be appreciated, the lid in step (f) constitutes a further component of the kit of parts according to the first aspect of the present invention as hereinbefore described. The tray and lid utilised preferably have one or more fold-lines formed therein, each said fold-line preferably being provided with reinforcement means in the form of a removable tab and associated cut-out section, located at each end of each said fold-line. Step (f) above preferably includes removing each said tab thereby to enable compacting of the tray and/or the lid.

In a preferred embodiment of the method according to the second aspect of the present invention, the medical equipment is a flexible medical endoscope. By utilising the method according to the second aspect of the present invention, it is believed that a satisfactory level of disinfection can be maintained for a period of up to 500 hours.

In order that the present invention may be more clearly understood, a preferred embodiment thereof will now be described in detail, though only by way of example, with reference to the accompanying drawings in which:

FIG. 8 is a perspective, exploded view of the tray, container, module and endoscope of FIG. 7, combined with a lid constituting a further component of a second major embodiment of a kit of parts according to a first aspect of the present invention.

Figure 1:
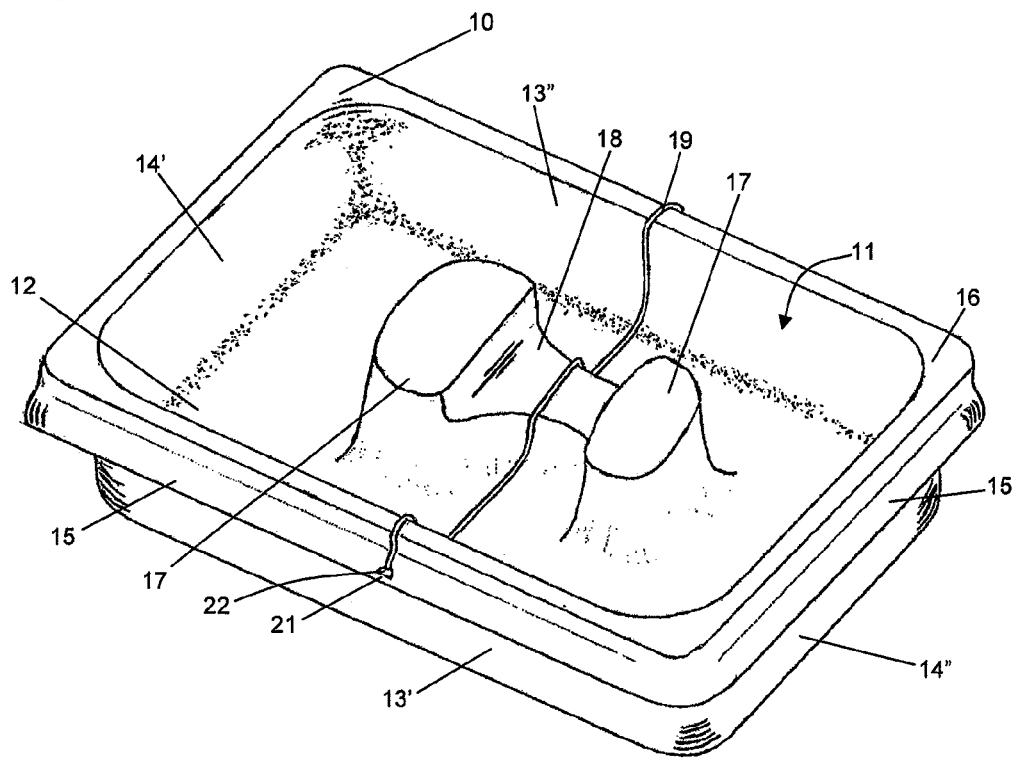
FIG. 1 is a perspective view of a tray constituting a principal component of a first major embodiment of a kit of parts according to a first aspect of the present invention.

Referring first to FIG. 1, there is shown a disposable tray 10, constituting a principal component of a first major embodiment of a kit of parts according to the present invention. The tray 10 has a downwardly-dished inner compartment, generally indicated 11 therewithin. The inner compartment 11 is defined by a base 12 having a generally rectangular outline, with a pair of opposed parallel side walls 13',13" and a pair of opposed parallel end walls 14',14" upstanding therefrom, said side walls 13 being perpendicular to said end walls 14.

The upper end of each wall 13, 14 is curled over to form a peripheral lip portion 15 extending externally around the walls 13, 14. A brim 16 around the inner compartment 11 is defined by the uppermost edge of the walls 13, 14.

The base 12 of the tray 10 has a pair of upstanding island structures 17 formed integrally therewith. As will be described in more detail below with reference to FIG. 4, the island structures 17 provide support and protection for the tubes of a flexible medical endoscope (not shown in FIG. 1) when placed in the tray 10. The island structures 17 are linked by a raised central region 18 of the base 12.

As can also be seen from FIG. 1, the tray 10 has a fold-line 19 formed therein to facilitate compaction of the tray 10 by breaking or folding, prior to disposal. The fold-line 19 runs from the peripheral lip portion 15 of the first side wall 13', over the brim 16 and down the internal surface of said first side wall 13', across the base 12 and over the raised central region 18 thereof, up the internal surface of the second opposed side wall 13", and over the brim 16 and onto the peripheral lip portion 15 of said second side wall 13". Throughout its course, the fold-line 19 runs in a straight line parallel to the opposed end walls 14. The fold-line 19 is provided at each end thereof with a reinforcement tab 21 and an associated cut-out section 22, as will be described in more detail below with reference to FIG. 3.

Figure 2:
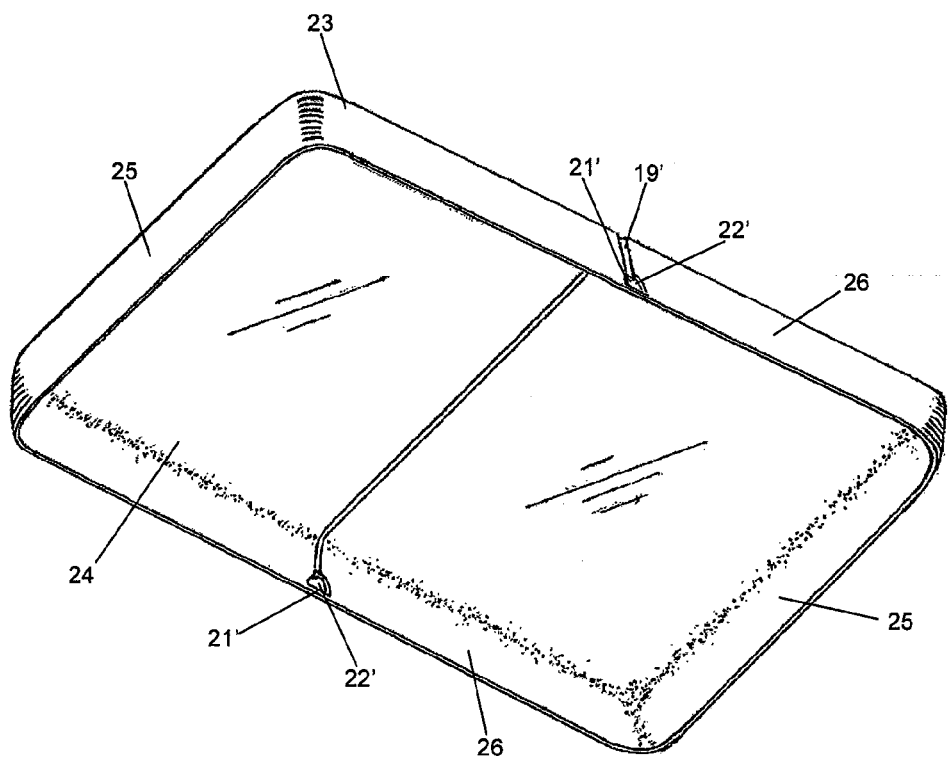
FIG. 2 is a perspective view of the underside of a lid constituting a further component of a first major embodiment of a kit of parts according to a first aspect of the present invention.

Referring now to FIG. 2, there is shown a disposable lid 23, constituting a further preferred component of the first major embodiment of a kit of parts according to the present invention, viewed from beneath. The lid 23 is adapted for engagement with the tray 10, and to this end is formed with a shape generally complementary to that of the tray 10. The lid 23 thus has a generally rectangular base section 24, with a pair of opposed end walls 25 and a pair of opposed side walls 26, depending therefrom. The end and side walls 25, 26 of the lid 23 are adapted to overlie and engage with the peripheral lip portions 15 of the tray 10, as can perhaps best be seen from FIG. 5. As will also be described in more detail below with reference to FIG. 5, the base section 24 of the lid 23 is constructed from clear plastics material, to enable viewing of the contents of the tray 10 when the lid 23 is in place.

Referring again to FIG. 2, the lid 23 has a fold-line 19' formed therein, similar to that formed in the tray 10. The lid fold-line 19' extends across the lid base 24 and down each opposed depending side wall 26, running in a straight line parallel to the opposed end walls 24. As with the tray 10, the fold-line 19' in the lid 23 is also provided at each end thereof with a reinforcement tab 21' and an associated cut-out section 22', as will be described in more detail below with reference to FIG. 3.

Figure 3:
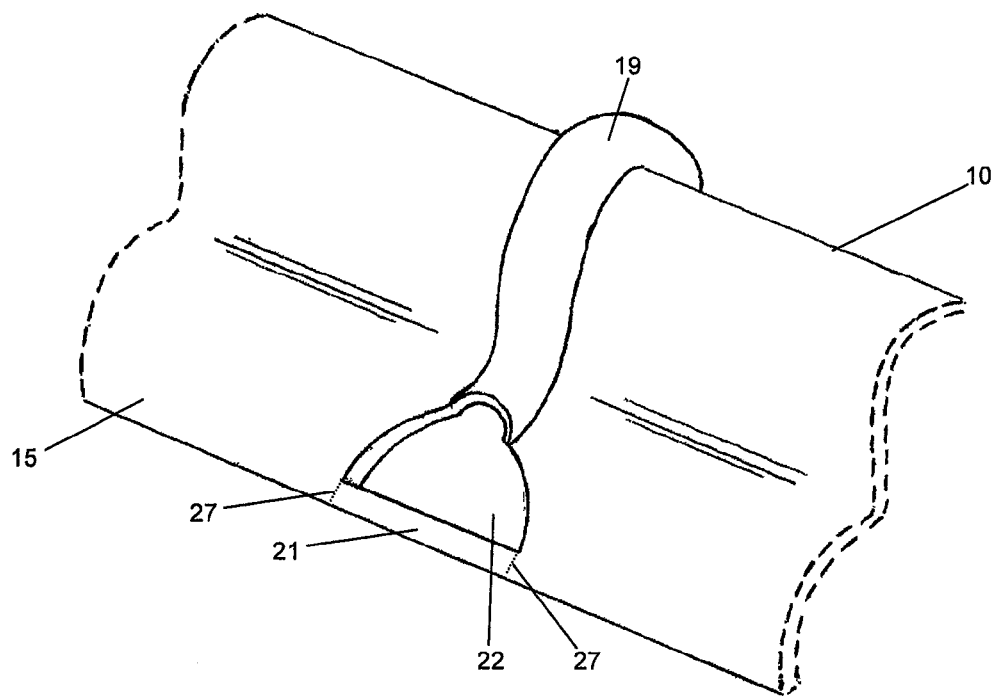
FIG. 3 is an enlarged view of a feature of the tray of FIG. 1.

Referring now to FIG. 3, there is shown an enlarged view of the reinforcement tab 21 and cut-out section 22 provided at each end of the fold-line 19 formed in the tray 10. Although described here with reference to the fold-line 19 in the tray 10, it will be appreciated that this description applies equally to the fold-line 19' formed in the lid 23. The fold-line 19 terminates at each end thereof in a cut-out section 22 of generally semi-circular shape, bound at its lower edge by a reinforcement tab 21. Each said tab 21 imparts strength and rigidity to the structure of the tray 10, thus preventing unintentional collapse of the tray 10 along the fold-line 19 when the tray is in use. Each tab 21 is defined between a pair of perforated break-lines 27 formed in the tray 10.

When the tray 10 is to be disposed of following use, each reinforcement tab 21 may be snapped off by breaking along the break-lines 27. This enables access to the cut-out section 22, and so facilitates the breaking or folding of the tray 10 along the fold-line 19. Once the tray 19 has been compacted by breaking or folding along the fold-line 19 it can then be disposed of in a standard hospital waste macerator.

Figure 4:
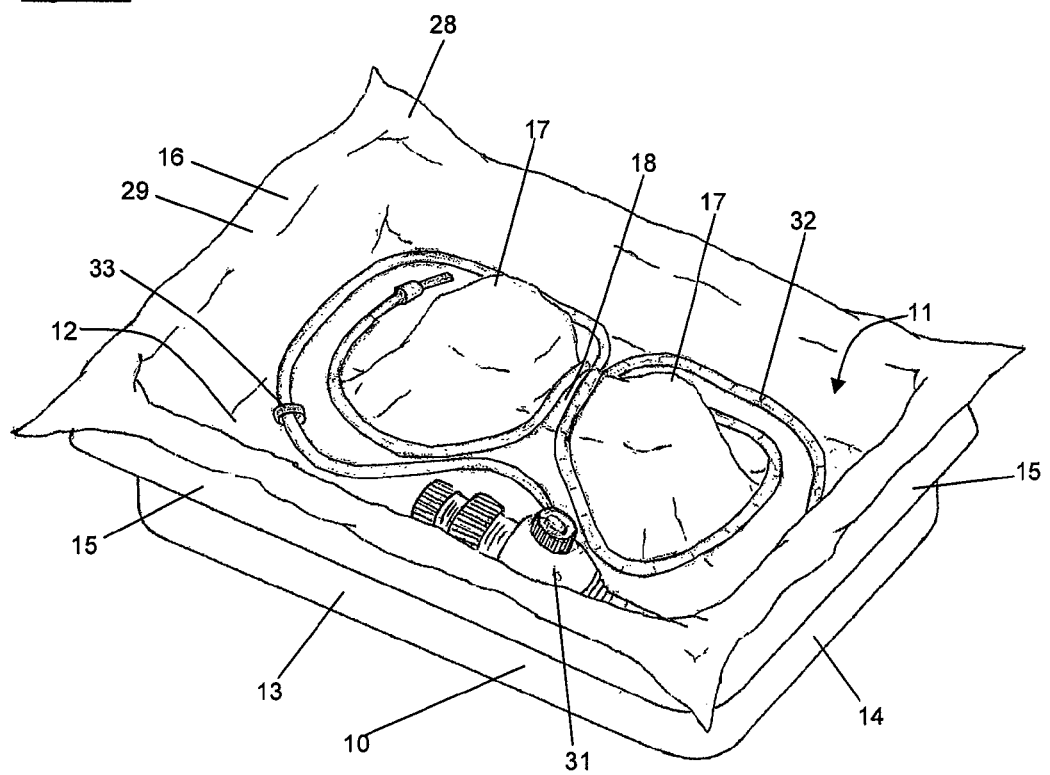
FIG. 4 is a perspective view of the tray of FIG. 1 in combination with a liner, constituting a further component of a first major embodiment of a kit of parts according to a first aspect of the present invention, in use with a flexible medical endoscope placed therein.

Referring now to FIG. 4, this shows the tray 10 lined with a disposable liner 28, constituting a further component of the first major embodiment of a kit of parts according to the present invention. The liner 28 is formed from flexible plastics materials and so conforms substantially to the shape of the tray 10, overlying the base 12, the upstanding island structures 17, and the raised central region 18. The margins 29 of the liner 28 are folded over the brim 16 to engage with the peripheral lip portions 15 of the walls 13, 14.

A flexible medical endoscope 31, in a disinfected condition having been subjected to processing, is placed in the tray 10, on top of the liner 28. The tubes 32 of the endoscope 31 are coiled around the island structures 17 and over the raised central region 18, so as to protect them during transit.

The endoscope 31 is provided with a status identification tag 33 to present a visual indication that the endoscope 31 is in a clean condition. Although not discernable from FIG. 4, this visual indication will generally be achieved by the tag 33 being green in colour, and/or having the word CLEAN printed thereon. The tag 33 is attached to the liner 28 and is looped around a tube 32 of the endoscope 31 to affix to itself or the liner 28 by means of a self-adhesive portion. When the endoscope 31 is to be used, the tag 33 must therefore be broken in order to separate the endoscope 31 from the liner 28. This provides a further fail-safe against the accidental use of contaminated endoscopes in surgical procedures, since the act of removing the tag 33 reinforces the message that the endoscope 31 is clean. Conversely, the absence of a tag 33 would immediately alert the operative to the possibility that the endoscope may be contaminated or at an unsatisfactory level of disinfection, and should be returned for further processing.

Similar status identification tags (not shown) may also be supplied in the kit to indicate that an endoscope is contaminated. These tags, which are to be attached following use of the endoscope 31 in a surgical procedure, would generally be coloured red, and/or have the word CONTAMINATED printed thereon, and need not be attached to a liner 28.

Figure 5:
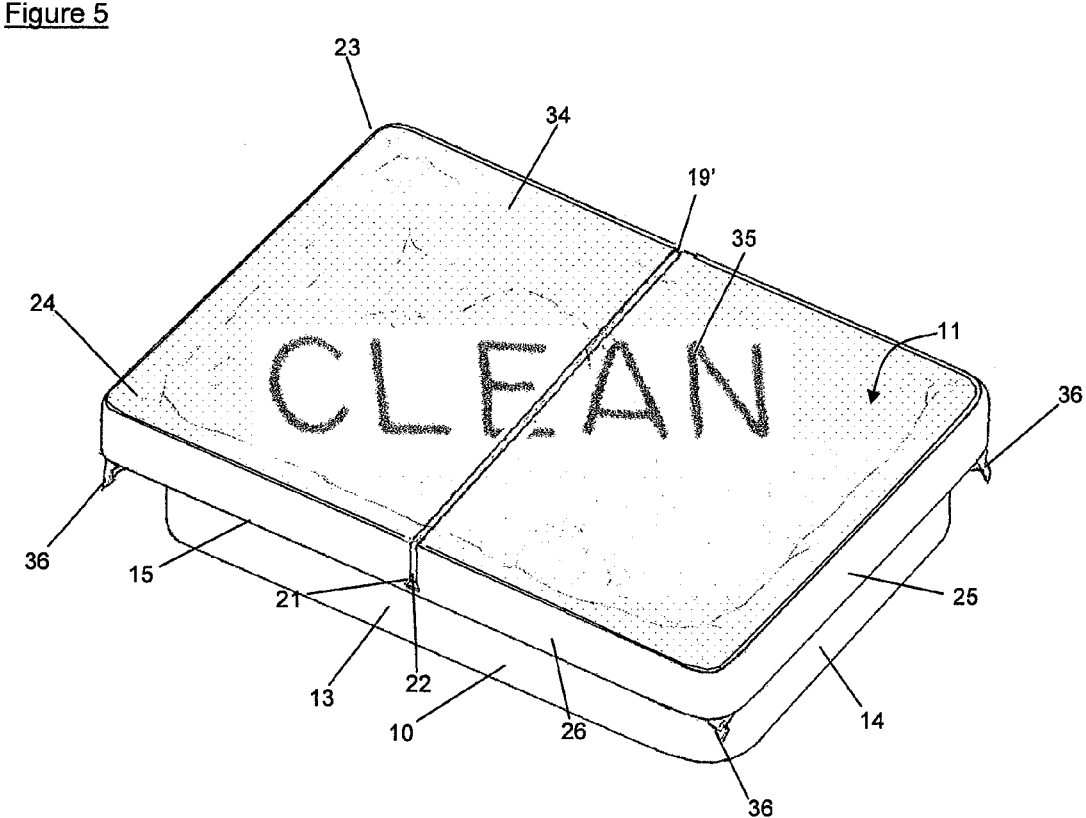
FIG. 5 is a perspective view of the tray and liner of FIG. 4, further combined with a protective cover constituting a further component of a first major embodiment of a kit of parts according to a first aspect of the present invention, and the lid of FIG. 2, in use with a flexible medical endoscope placed therein.

Referring now to FIG. 5, this shows the above described tray 10 and liner 28 combination, now further combined with a disposable cover 34, constituting a further component of the first major embodiment of a kit of parts according to the present invention, and the above described lid 23. The disposable cover 34 is added to the above described tray 10 and liner 28 combination, after having placed the processed endoscope 31 (not visible in FIG. 5) in the lined compartment 11. The cover 34 carries a disinfection status indicator 35 to provide a further visual indication of the disinfection status of the endoscope 31, so that the status of the contents can be easily identified during transit. This is again achieved by making the cover 34 green in colour and/or having the word CLEAN printed thereon, as shown in FIG. 5.

The kit of the present invention may desirably also include a further cover (not shown) intended to be used following use of the endoscope 31 in a surgical procedure, to provide a visual indication that the contents are contaminated. This is achieved by making this cover red in colour and/or having the word CONTAMINATED printed thereon. Alternatively, a single reversible cover 34 may be provided, having the clean and contaminated status indicators on respective opposite faces thereof.

The cover 34 is adapted to be retained on the tray 10 by engaging the peripheral lip portions 15 of the walls 13, 14 of the tray 10. In order to facilitate attachment and removal of the cover 34, a manually graspable ear 36 is provided at each corner thereof.

As described above, the base section 24 of the lid 23 is formed from clear plastics material. When the lid 23 is in place over the cover 34, with the depending walls 25, 26 of the lid embracing the peripheral lip portions 15 of the tray 10, the clear lid base 24 acts as a window to enable the disinfection status indicator 35 carried on the cover 34 to be viewed. The disinfection status of the endoscope 31 can thus be assessed without needing to remove the lid 23, which would run the risk of exposing a clean endoscope 31 to potential contamination.

Figure 6:
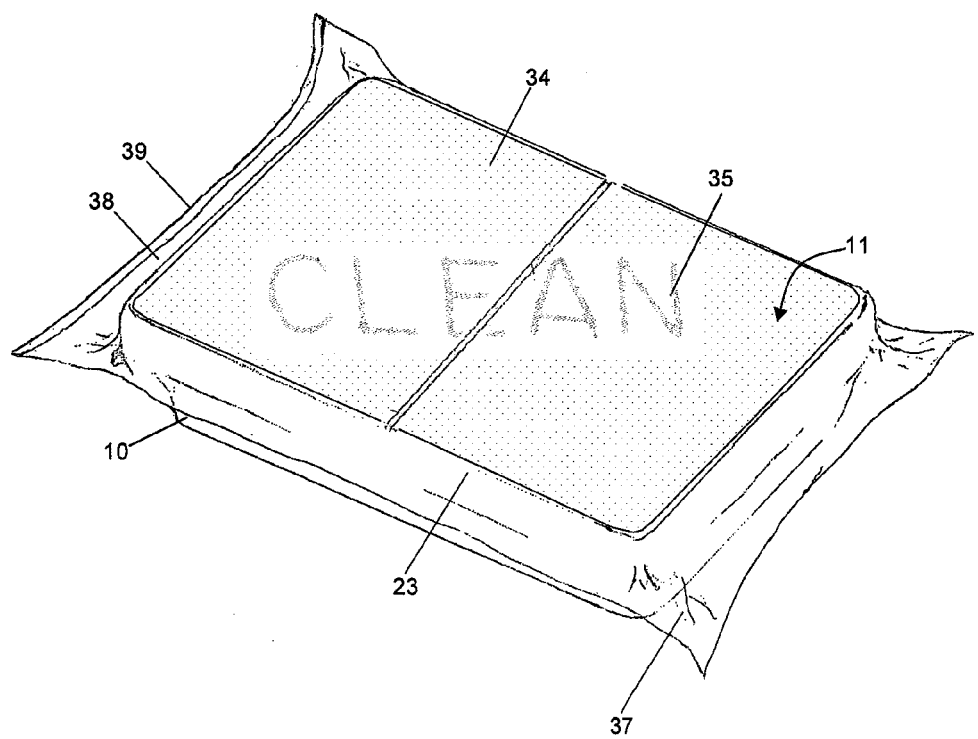
FIG. 6 is a perspective view of the tray, liner, cover and lid of FIG. 5, further combined with an oxygen-impermeable container constituting a further component of a first major embodiment of a kit of parts according to a first aspect of the present invention.

Referring now to FIG. 6, this shows the above described tray 10, in combination with the liner 28, cover 34 and lid 23 (though not all of these components are visible in FIG. 6), housed within an oxygen-impermeable container 37, constituting a further component of the first major embodiment of a kit of parts according to the present invention.

Following processing of the endoscope 31, the loaded tray 10, complete with liner 28, endoscope 31, cover 34 and lid 23 is placed into the container 37 via an opening at one end 38 thereof. This end 38 of the container 37 is adapted for sealing by forming a heat seal 39, or may alternatively be provided with a zip closure. The heat seal 39 may be further reinforced by the addition of a full-width clamping clip (not shown). The container 37 is evacuated by electrical, mechanical or manual suction means so as to reduce the pressure within the inner compartment 11. The evacuation of the container 37 deprives aerobic micro-organisms within the compartment 11 of oxygen, so reducing or preventing their multiplication. Additionally, the reduced pressure promotes evaporation of residual moisture in the compartment, thus depriving micro-organisms of an essential solvent for nutrients, again so as to reduce or eliminate multiplication.

The inner compartment 11 may desirably also be provided with sachets (not shown) of oxygen scavengers and desiccants to further enhance this effect. The container 37 may also be charged with a disinfectant gas or vapour such as sterile isopropanol gas. As can also be seen in FIG. 6, the container 37 is formed from clear plastics material to enable the disinfection status indicator 35 on the cover 34 to be viewed through the container 37 and the lid 23.

Figure 7:
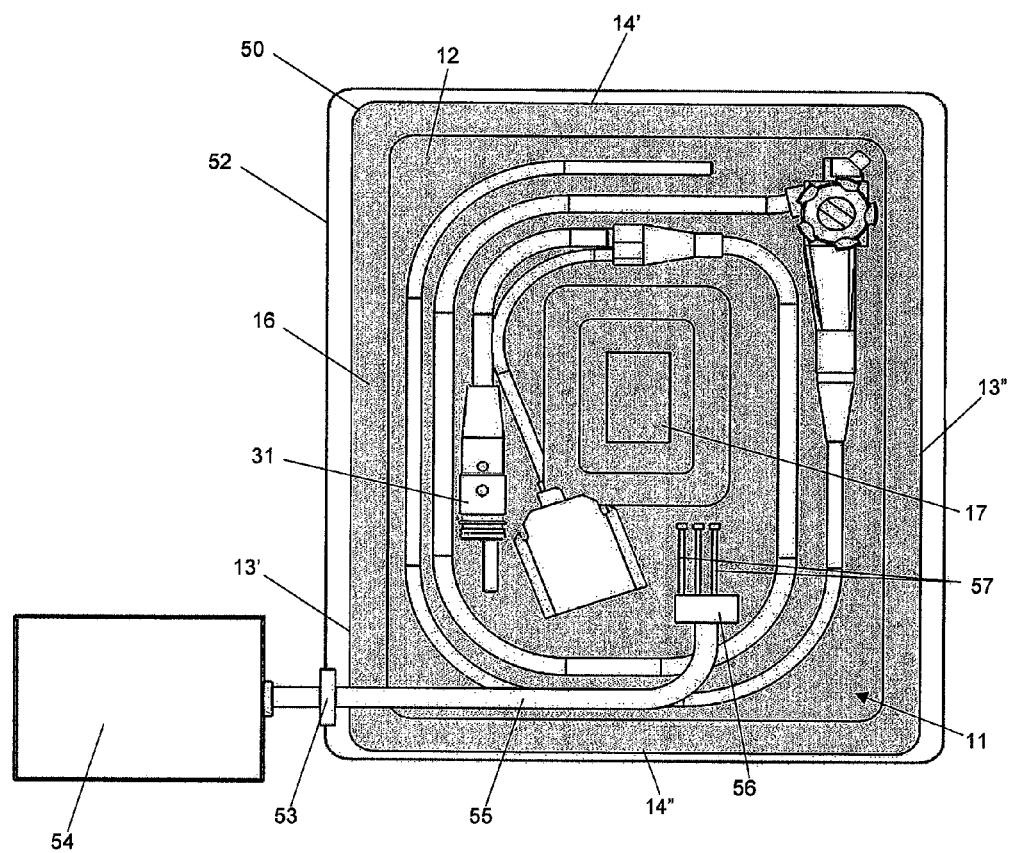
FIG. 7 is an internal plan view of a combined tray, oxygen-impermeable container and control module, constituting components of a second major embodiment of a kit of parts according to a first aspect of the present invention, in use with a flexible medical endoscope placed therein.

Referring now to FIGS. 7 and 8, there are shown several constituent components of a second major embodiment of a kit of parts according to the present invention. A disposable tray 50, constituting a principal component of said second embodiment is provided, said tray 50 being similar in configuration to the tray 10 of the first embodiment described above with reference to FIGS. 1 to 6, in that it comprises a base 12, a pair of opposed parallel side walls 13',13" and a pair of opposed parallel end walls 14',14" upstanding from said base 12, and a brim 16 defined by the uppermost edge of said walls 13,14. The tray 50 also has a generally central island structure 17 formed integrally with the base 12 and upstanding therefrom.

The tray 50 of the second embodiment differs from the tray 10 of the first embodiment inter alia in that it is somewhat shallower. As can be seen in FIG. 8, the tray 50 is intended to be combined with a complementarily shaped lid 51 to form a tray assembly; each of the tray 50 and lid constituting substantially one half of said assembly. Thus, in the second embodiment, the inner compartment 11 within which the flexible medical endoscope 31 is housed is effectively defined between the tray 50 and lid 51, rather than by the structure of the tray alone, as in the first embodiment.

The tray 50 of the second embodiment is shown in FIGS. 7 and 8 in combination with an oxygen-impermeable container 52, the construction and function of which are broadly similar to that of the container 37 of the first embodiment described above with reference to FIG. 6. However, the container 52 of the second embodiment differs from the container 37 of the first embodiment in that it is provided with a port 53 in one wall thereof. The port 53 enables a control module 54, constituting a further component of the second embodiment of a kit of parts according to the present invention, to access the inner compartment 11 within which the endoscope 31 is housed.

The control module 54 communicates with the inner compartment 11 via a length of flexible tubing 55, at the distal end of which is located a hub 56 having connectors 57 adapted for attachment to the internal channels of the flexible medical endoscope 31. The port 53 is provided with one or more valves (not shown) to allow communication of the inner compartment 11 with the ambient atmosphere. These valves can be used to aspirate the internal channels of the endoscope 31 following the partial evacuation of the inner compartment 11, as described above with reference to FIG. 6. When the one or more valves in the port 53 are opened, the pressure difference between the inner compartment 11 and the ambient atmosphere causes air to be drawn through the port 53, tubing 55 and connectors 57, and into the internal channels of the endoscope 31, to flush out any residual moisture. The port 53 is also provided with a high efficiency particulate air (HEPA) filter (not shown) to remove particulate matter and moisture from the air as it is drawn through the port 53. The port 53 may also be provided with, or in communication with, an ultraviolet light source, an ozone generator, and a sound wave generator, each of which may be used to impart further disinfection or sterilisation to the inner compartment 11.

The operation of the one or more valves in the port 53 (and the optional disinfection or sterilisation devices described above, if present) is controlled by the control module 54, which includes an embedded micro-processor. The control module 54 is also used to control the pressure-reducing and gas-charging steps of the method according to the second aspect of the present invention, as described above with reference to FIG. 6. The operation of the atmospheric valve and the pressure-reducing and gas-charging steps may be carried out repeatedly, intermittently and in varying orders to promote the removal of residual moisture from the internal channels of the endoscope 31. The control module 54 may also be adapted to monitor the atmospheric pressure, the pressure and humidity levels with the container 52, and the elapsed time for each method step, and to communicate appropriate operational data to a remote display (not shown). The control module 54 may also be further adapted to generate an audible or visual alarm in the event of a fault.

Referring now to FIG. 8, it can be seen that the tray 50 and lid 51 are each formed with a cellular structure 58. This serves to impart rigidity to the tray 50 and lid 51 drawing use but facilitates compaction of the tray 50 and lid 51 after use. The cellular structure 58 also enables the tray 50 and lid 51 partially to deform upon the reduction of pressure in the container 52, as described above with reference to FIG. 6. This causes the endoscope 31 within the inner compartment 11 to be grasped firmly between the tray 50 and lid 51 so as to prevent unwanted movement or vibration of the endoscope 31 during transit. As can also be seen from FIG. 8, the tray 50 is provided with a pair of fold lines 19, whilst the lid 51 is provided with a pair of fold lines 19', to facilitate compaction after use, as described above with reference to FIGS. 1 and 2.

The invention claimed is:

1. A medical equipment storage and transportation kit adapted for the storage and, transportation of medical equipment following processing or use thereof, said kit comprising:
   a tray defined by a base and surrounding walls, upper ends of the surrounding walls forming a peripheral lip portion that extends externally around the surrounding walls, said tray having at least one fold-line formed therein, the fold-line running from the peripheral lip portion, down a first wall, across the base, up a second wall and onto the peripheral lip portion, thereby to facilitate compaction of said tray for disposal; and
   a lid adapted to engage with the walls of the tray, and having at least one fold-line formed therein;
   wherein each said fold-line terminates at each end thereof in a cut-out section bound at one edge thereof by a reinforcement tab, thereby to prevent unintentional collapse of the tray and lid along the fold-line when said kit is in use; and wherein each said reinforcement tab is removable to facilitate folding of the tray and lid along each said fold-line for compaction and disposal, following use of said kit;
   and optionally one or more of:
   a tray liner;
   a protective cover adapted to be detachably secured to the tray; and
   an oxygen-impermeable container adapted to receive said tray therewithin.

2. The medical equipment storage and transportation kit as claimed in claim 1, wherein:
   the tray has an inner compartment defined by the base and surrounding walls;
   the tray liner is present and is adapted to line the inner compartment of the tray; and
   the protective cover is present and is adapted to be extended across the inner compartment.

3. The medical equipment storage and transportation kit as claimed in claim 1, wherein at least one of the tray and the lid has in the range of from one to three fold-lines formed therein.

4. The medical equipment storage and transportation kit as claimed in claim 1, wherein at least one of the tray and the lid is provided with at least one upstanding island structure.

5. The medical equipment storage and transportation kit as claimed in claim 1, comprising a pair of interchangeable protective covers, one member of said pair of covers carrying an indicator adapted to provide a visual indication that medical equipment contained within said inner compartment is clean, and the other member of said pair carrying an indicator adapted to provide a visual indication that said medical equipment is contaminated.

6. The medical equipment storage and transportation kit as claimed in claim 1, wherein at least one of the tray and the lid is formed from paper pulp material treated with an additive adapted to render the material water resistant.

7. The medical equipment storage and transportation kit as claimed in claim 1, wherein at least one of the tray and the lid is formed at least partially from transparent plastics material.

8. The medical equipment storage and transportation kit as claimed in claim 1, further comprising at least one contaminated status indication tag for attachment to medical equipment following use, and at least one clean status indication tag adapted for attachment to medical equipment within the tray, said tags being adapted to provide a visual indication as to said medical equipment's status.

9. The medical equipment storage and transportation kit as claimed in claim 1, adapted for storage and transportation of a flexible medical endoscope.

10. The medical equipment storage and transportation kit as claimed in claim 1, wherein the dimensions of the lid are substantially equal to those of the tray, and wherein the lid is formed with a structure and profile complementary to that of the tray, such that when the lid is engaged with the tray, each said component constitutes substantially one half of a tray assembly, and wherein an inner compartment adapted to receive an article of medical equipment is defined between said tray and said lid.

11. The medical equipment storage and transportation kit as claimed in claim 10, wherein the tray and the lid are each formed with a cellular structure to facilitate compaction following use.

12. The medical equipment storage and transportation kit as clamed in claim 10, wherein the oxygen-impermeable container is present, and is provided with a port adapted to communicate with the inner compartment of the tray assembly via at least one flexible tube, at least one of said tray and said lid being shaped so as to permit access of said at least one flexible tube to said inner compartment when the lid is engaged with the tray.

13. The medical equipment storage and transportation kit as claimed in claim 12, wherein said at least one flexible tube is adapted to communicate with internal channels of a flexible medical endoscope when housed within the inner compartment of the tray assembly.

14. The medical equipment storage and transportation kit as claimed in claim 12, further comprising a control module in communication with said container port and adapted to monitor and control the container's internal environment.

15. A method for maintaining the disinfection of medical equipment following processing thereof, utilising a kit of parts as claimed in claim 1, comprising the following major steps:
  (a) placing disinfected medical equipment in a tray with a lid, said tray and lid constituting principal components of a kit of parts as claimed in claim 1;
  (b) placing said loaded tray in an oxygen-impermeable container;
  (c) sealing the container;
  (d) reducing pressure within the container by a suction process selected from mechanical, electrical and manual suction; and
  (e) removing atmospheric oxygen from the container by a gas scavenger.

16. The method as claimed in claim 15, further comprising the preliminary step, prior to performing major step (a), of:
  (i) attaching to the medical equipment at least one clean status indication tag to provide a visual indication that said medical equipment is clean.

17. The method as claimed in claim 15, further comprising an additional step, prior to performing major step (e), of:
  (ii) charging the container with a disinfectant gas or vapor.

18. The method as claimed in claim 15, comprising, following use of the medical equipment in a medical procedure and the subsequent transportation of said equipment for processing, the further major steps of:
  (f) compacting the tray and the lid by folding along each said fold-line; and
  (g) disposing of the compacted tray and the lid.

* * * * *